US008962117B2

(12) United States Patent
Belfadhel et al.

(10) Patent No.: US 8,962,117 B2
(45) Date of Patent: Feb. 24, 2015

(54) PROCESS FOR PRODUCING BISPHENOL A WITH REDUCED SULFUR CONTENT, POLYCARBONATE MADE FROM THE BISPHENOL A, AND CONTAINERS FORMED FROM THE POLYCARBONATE (71) Applicants: Hatem Abdallah Belfadhel, Roosendaal (NL); Johannes de Brouwer, Oisterwijk (NL); Marcel Vieveen, De Heen (NL); Christian Wold, Halsteren (NL); Eric Brander, Tholen (NL)

(72) Inventors: Hatem Abdallah Belfadhel, Roosendaal (NL); Johannes de Brouwer, Oisterwijk (NL); Marcel Vieveen, De Heen (NL); Christian Wold, Halsteren (NL); Eric Brander, Tholen (NL)

(73) Assignee: Sabic Global Technologies B.V. (NL)

( * ) Notice: Subject to any disclaimer, the term of this patent is extended or adjusted under 35 U.S.C. 154(b) by 362 days.

(21) Appl. No.: 13/660,195

(22) Filed: Oct. 25, 2012

(65) Prior Publication Data
US 2013/0108820 A1 May 2, 2013

Related U.S. Application Data (60) Provisional application No. 61/552,191, filed on Oct. 27, 2011, provisional application No. 61/552,189, filed on Oct. 27, 2011.

(51) Int. Cl.
*B29D 22/00* (2006.01)
*B29D 23/00* (2006.01)
(Continued)

(52) U.S. Cl.
CPC .............. *C07C 37/685* (2013.01); *C08G 64/04* (2013.01); *C07C 37/68* (2013.01); *C07C 39/16* (2013.01);
(Continued)

(58) Field of Classification Search
CPC ........ C07C 37/20; C07C 37/68; C07C 39/16; C07C 37/685; C08G 64/04; B29D 22/00; B29D 23/00; B32B 1/08
USPC .......................... 428/36.92; 568/724; 528/196
See application file for complete search history.

(56) References Cited

U.S. PATENT DOCUMENTS 3,839,247 A  10/1974 Bialous et al.
4,076,686 A   2/1978 Calkins
(Continued)

FOREIGN PATENT DOCUMENTS

CN     101205358 A     6/2008
CN     101885907 A    11/2010
(Continued)

OTHER PUBLICATIONS

Chan et al., "Facile Quantitative Analysis of Hydroxyl End Groups of Poly (2,6-dimethyl-1,4-phenylene oxide)s by 31P NMR Spectroscopy", Macromolecules (1994), vol. 27, pp. 6371-6375.
(Continued)

*Primary Examiner* — Michael C Miggins
(74) *Attorney, Agent, or Firm* — Cantor Colburn LLP (57) ABSTRACT In one embodiment, a process for producing a bisphenol A product comprises: reacting phenol with acetone in the presence of a sulfur containing promoter to obtain a reaction mixture comprising bisphenol A, phenol, and the promoter; after reacting the phenol with the acetone, cooling to form a crystal stream comprising crystals of bisphenol A and phenol; separating the crystals from the crystal steam; melting the crystals to form a molten stream of bisphenol A, phenol, and sulfur; contacting the molten stream with a base to reduce a sulfur concentration in the molten stream and form a reduced sulfur stream; and removing phenol from the reduced sulfur stream to form a bisphenol A product. Also disclosed herein is a container comprising: a polycarbonate formed from a bisphenol A having a sulfur concentration of 0.5 to 15 ppm based upon the weight of the bisphenol A.

26 Claims, 4 Drawing Sheets (51) Int. Cl.
*B32B 1/08* (2006.01)
*C07C 37/68* (2006.01)
*C07C 37/20* (2006.01)
*C07C 37/82* (2006.01)
*C07C 37/86* (2006.01)
*C08G 64/04* (2006.01)
*C07C 39/16* (2006.01)

(52) U.S. Cl.
CPC . *B29D 22/00* (2013.01); *B32B 1/08* (2013.01); *B29D 23/00* (2013.01); *C07C 37/20* (2013.01); *C07C 37/82* (2013.01); *C07C 37/86* (2013.01)
USPC .................. 428/36.92; 568/724; 528/196

(56) References Cited

U.S. PATENT DOCUMENTS

| | | |
|---|---|---|
| 5,064,885 A | 11/1991 | Muller et al. |
| 5,288,926 A | 2/1994 | Patrascu et al. |
| 5,364,895 A | 11/1994 | Stevenson et al. |
| 5,424,006 A | 6/1995 | Murayama et al. |
| 5,438,086 A | 8/1995 | Stevenson et al. |
| 5,470,938 A | 11/1995 | Sakashita et al. |
| 5,672,664 A | 9/1997 | DeRudder et al. |
| 5,883,218 A | 3/1999 | Gordon et al. |
| 6,066,861 A | 5/2000 | Hohn et al. |
| 6,069,225 A | 5/2000 | Gerace et al. |
| 6,174,987 B1 | 1/2001 | Gordon et al. |
| 6,512,148 B1 | 1/2003 | Yamamoto et al. |
| 6,613,823 B1 | 9/2003 | Battiste et al. |
| 6,692,659 B2 | 2/2004 | Brown et al. |
| 6,706,846 B2 | 3/2004 | Brack et al. |
| 6,995,294 B2 | 2/2006 | Webb et al. |
| 7,112,703 B2 | 9/2006 | Neumann et al. |
| 7,227,046 B2 | 6/2007 | Commarieu |
| 7,491,837 B2 | 2/2009 | Schlosberg et al. |
| 7,852,428 B2 | 12/2010 | Byoun et al. |
| 7,879,927 B2 | 2/2011 | Vlottes et al. |
| 7,959,827 B2 | 6/2011 | Comanzo et al. |
| 7,964,273 B2 | 6/2011 | Kogure et al. |
| 7,989,531 B2 | 8/2011 | Bersted et al. |
| 2002/0147256 A1 | 10/2002 | Eckel et al. |
| 2003/0180542 A1 | 9/2003 | Pickett et al. |
| 2004/0227465 A1 | 11/2004 | Menkara et al. |
| 2005/0113534 A1 | 5/2005 | Agarwal et al. |
| 2005/0177007 A1 | 8/2005 | Neumann et al. |
| 2005/0215833 A1 | 9/2005 | Neumann et al. |
| 2006/0135690 A1 | 6/2006 | Juikar et al. |
| 2006/0263547 A1 | 11/2006 | Cojocariu et al. |
| 2007/0004941 A1 | 1/2007 | Blaschke et al. |
| 2007/0139949 A1 | 6/2007 | Tanda et al. |
| 2007/0299169 A1 | 12/2007 | Ohira et al. |
| 2008/0029720 A1 | 2/2008 | Li |
| 2008/0081855 A1 | 4/2008 | Mullen |
| 2008/0113117 A1 | 5/2008 | Coenjarts et al. |
| 2009/0043053 A1 | 2/2009 | Gorney et al. |
| 2009/0054586 A1 | 2/2009 | Hein et al. |
| 2010/0137549 A1 | 6/2010 | Takahashi et al. |
| 2011/0127904 A1 | 6/2011 | Tsai |
| 2011/0140593 A1 | 6/2011 | Negley et al. |
| 2011/0151262 A1 | 6/2011 | Heuer et al. |
| 2011/0278614 A1 | 11/2011 | Maier-Richter et al. |
| 2012/0043552 A1 | 2/2012 | David et al. |
| 2013/0094179 A1 | 4/2013 | Dai et al. |
| 2013/0108820 A1 | 5/2013 | Belfadhel et al. |
| 2013/0221837 A1 | 8/2013 | De Brouwer et al. |
| 2013/0270591 A1 | 10/2013 | De Brouwer et al. |
| 2014/0051802 A1 | 2/2014 | De Brouwer et al. |
| 2014/0051803 A1 | 2/2014 | De Brouwer et al. |

FOREIGN PATENT DOCUMENTS

| | | |
|---|---|---|
| CN | 102134383 A | 7/2011 |
| CN | 202091807 U | 12/2011 |
| DE | 102006016548 A1 | 10/2006 |
| EP | 0320658 A1 | 6/1989 |
| EP | 0475893 A1 | 3/1992 |
| EP | 0523931 A2 | 1/1993 |
| EP | 0885929 A1 | 12/1998 |
| EP | 1234845 A2 | 8/2002 |
| EP | 1500671 A1 | 1/2005 |
| EP | 1808726 A1 | 7/2007 |
| EP | 1925874 A1 | 5/2008 |
| EP | 2143750 A1 | 1/2010 |
| EP | 2248841 A1 | 11/2010 |
| GB | 1377227 A | 12/1974 |
| JP | 2004149623 A | 5/2004 |
| JP | 2004231935 A | 8/2004 |
| JP | 2005037591 A | 2/2005 |
| JP | 2005048154 A | 2/2005 |
| JP | 2005082713 A | 3/2005 |
| JP | 2005115051 A | 4/2005 |
| JP | 2006339033 A | 12/2006 |
| JP | 2008184482 A | 8/2008 |
| JP | 2011029051 A | 2/2011 |
| KR | 20110033772 A | 3/2011 |
| WO | 9209550 A1 | 6/1992 |
| WO | 0059853 A1 | 10/2000 |
| WO | 2011082204 A1 | 7/2011 |
| WO | 2011134674 A1 | 11/2011 |
| WO | 2012150559 A1 | 11/2012 |
| WO | 2013021332 A1 | 2/2013 |
| WO | 2013061274 A1 | 5/2013 |

OTHER PUBLICATIONS

Chinese Patent No. 202091807 (U); Publication Date: Dec. 28, 2011; Abstract Only; 1 Page.
Japanese Patent No. 2005082713 (A); Publication Date: Mar. 31, 2005; Abstract Only; 2 Pages.
Liptak et al.; "Absolute pKa Determination for Substituted Phenols"; J. Am. Chem. Soc.; vol. 124; 2002; pp. 6421-6427.
Chou et al.; "The Optimum Conditions for Solid-State-Prepared (Y3-xCex)Al5O12 Phosphor Using the Taguchi Method"; Advanced Powder Technology; vol. 12; 2012; pp. 97-103.
Chinese Patent No. 101205358 (A); Publication Date: Jun. 6, 2008; Abstract Only; 1 Page.
Chinese Patent No. 101885907 (A); Publication Date: Nov. 17, 2010; Abstract Only; 1 Page.
Chinese Patent No. 102134383 (A); Publication Date: Jul. 27, 2011; Abstract Only; 1 Page.
Japanese Patent No. 2004149623 (A); Publication Date: May 27, 2004; Abstract Only; 1 Page.
Japanese Patent No. 2004231935 (A); Publication Date: Aug. 19, 2004; Abstract Only; 1 Page.
Japanese Patent No. 2005037591 (A); Publication Date: Feb. 10, 2005; Abstract Only; 2 Pages.
Japanese Patent No. 2005048154 (A); Publication Date: Feb. 24, 2005; Abstract Only; 1 Page.
Japanese Patent No. 2005115051 (A); Publication Date: Apr. 28, 2005; Abstract Only; 1 Page.
Japanese Patent No. 2006339033 (A); Publication Date: Dec. 14, 2006; Abstract Only; 2 Pages.
Japanese Patent No. 2008184482 (A); Publication Date: Aug. 14, 2008; Abstract Only; 1 Page.
Japanese Patent No. 2011029051 (A); Publication Date: Feb. 10, 2011; Abstract Only; 2 Pages.
Anderson et al.; "Quantitative Analysis of Commercial Bisphenol A by Paper Chromatography"; Analytical Chemistry; vol. 31, No. 7; 1959; p. 1214-1217.
Brunelle, D.J.: "Polycarbonates", Encyclopedia of Polymer Science and Technology, Jan. 1, 2006, pp. I.1-33, XP002525090, DOI: 10.1002/0471440264PST255.PUB2, Retrieved from the Internet: URL:http://mrw.interscience. wiley.com/emrw/9780471440260/epst/article/pst255/current/abstract.
Brydia; "Determination of Bisphenol A and Impurities by Gas Chromatography of Their Trimethylsilyl Ether Derivatives" Analytical Chemistry; vol. 40, No. 14; 1968; pp. 2212-2215.
De Brouwer et al.; "Lexan* Polycarbonate for Optical Applications"; SABIC Innovative Plsatics; Received Aug. 2, 2011; 5 Pages.

(56) References Cited

OTHER PUBLICATIONS

Factor; "Search for the Sources of Color in Thermally Aged, Weathered and y-Ray Irradiated Bisphenol A Polycarbonate"; Die Angewandte Makromolekulare Chemie; vol. 232; 1995; pp. 27-43.

Factor et al.; "The Use of 31P NMR to Identify Color Bodies in y-irradiated Bisphenol-A Polycarbonate*"; Polymer Degradation and Stability; vol. 57; 1997; pp. 83-86.

Godinez et al.; "Experimental Study of the Influence of Raw Material Impurities on Yellowness Index of Transesterification Polycarbonate"; Journal of Applied Polymer Science; vol. 119; 2011; pp. 1348-1356.

Li et al.; "Design of Mechanically Robust High-Tg Polymers: Synthesis and Dynamic Machanical Relaxation Behavior of Glassy Poly(ester carbonate)s with Cyclohexylene Rings in the Backbone"; Macromolecules; vol. 36; 2003; pp. 9411-9420.

Poskrobko et al.; "High-Performance Liquid Chromatography wtih Multi-Wavelength Detection of the Bisphenol A Impurities"; Journal of Chromatography A; vol. 883; 2000; pp. 291-297.

International Search Report for International Application No. PCT/IB2012/055880; International Filing Date Oct. 25, 2012; Date of Mailing Feb. 13, 2013; 5 pages.

Written Opinion of the International Search Report for International Application No. PCT/IB2012/055880; International Filing Date Oct. 25, 2012; Date of Mailing Feb. 13, 2013; 11 pages.

Nowakowska et al.; "Studies of Some Impurities in Commercial Bisphenol-A"; Polish Journal of Applied Chemistry; vol. 3; 1996; pp. 247-254.

PROCESS FOR PRODUCING BISPHENOL A WITH REDUCED SULFUR CONTENT, POLYCARBONATE MADE FROM THE BISPHENOL A, AND CONTAINERS FORMED FROM THE POLYCARBONATE

CROSS REFERENCE TO RELATED APPLICATIONS

The present application claim priority to U.S. Provisional Application Ser. No. 61/552,191, filed on Oct. 27, 2011, and U.S. Provisional Application Ser. No. 61/552,189, filed on Oct. 27, 2011, the contents of which is hereby incorporated by reference.

BACKGROUND

This disclosure relates to a container formed from polycarbonate, wherein the polycarbonate was produced from 2,2-bis(4-hydroxyphenyl)propane (bisphenol A, BPA) with reduced sulfur content, and to a process for producing the bisphenol A.

BPA is widely employed in the manufacture of polymeric materials, such as engineering thermoplastics. For example, BPA is a principle monomer used in the manufacture of polycarbonate. In order to be effective in producing high quality polycarbonate products, high purity levels are needed of the raw material BPA.

Bisphenols, such as BPA, are generally prepared by the electrophilic addition of aldehydes, or ketones such as acetone, to aromatic hydroxyl compounds such as phenol, in the presence of an acidic catalyst. These types of reactions are also referred to as acid catalyzed condensation reactions.

There is a long felt yet unsatisfied need for new and improved processes for producing bisphenol A, which processes could, for example, employ a sulfur containing promoter in the reaction due to its ability to increase reaction conversion and improve selectivity in producing BPA. There is further a need for polycarbonate products such as containers, having a reduced sulfur content.

BRIEF DESCRIPTION

Herein, disclosed are processes for producing high quality bisphenol A with reduced sulfur content, and also disclosed are polycarbonate containers comprising sulfur in a low concentration.

In one embodiment, a process for producing a bisphenol A product comprises: reacting phenol with acetone in the presence of a sulfur containing promoter to obtain a reaction mixture comprising bisphenol A, phenol, and the promoter; after reacting the phenol with the acetone, cooling the reaction mixture to form a crystal stream comprising crystals of bisphenol A and phenol; separating the crystals from the crystal steam; melting the crystals to form a molten stream of bisphenol A, phenol, and sulfur; contacting the molten stream with a base to reduce a sulfur concentration in the molten stream and form a reduced sulfur stream; and removing phenol from the reduced sulfur stream to form a bisphenol A product.

In one embodiment, a process for making polycarbonate, comprises: reacting, in the presence of a transesterification catalyst, a diaryl carbonate ester and a bisphenol A, wherein the bisphenol A has a sulfur concentration of 0.5 ppm to 15 ppm, based upon a weight of the bisphenol A.

In another embodiment, a process for making polycarbonate, comprises: forming a mixture of bisphenol A in aqueous caustic material, wherein the bisphenol A has a sulfur concentration of 0.5 ppm to 15 ppm, based upon a weight of the bisphenol A; adding the mixture to a water-immiscible solvent medium; and contacting the reactants with a carbonate precursor in the presence of a catalyst to form the polycarbonate.

In one embodiment, a container comprises: a polycarbonate formed from a bisphenol A having a sulfur concentration of 0.5 to 15 ppm based upon a weight of the bisphenol A.

The above described and other features are exemplified by the following figures and detailed description.

BRIEF DESCRIPTION OF THE DRAWINGS

Refer now to the figures, which are exemplary and non-limiting embodiments, and wherein the like elements are numbered alike.

DETAILED DESCRIPTION

Bisphenol A can be obtained by reacting acetone and phenol in the presence of a strong acid catalyst, such as hydrochloric acid (HCl) or a sulfonic resin and a sulfur containing promoter, e.g., a mercaptan promoter, such as methyl mercaptan (MM), ethyl mercaptan, 2,2-bis(methylthio)propane, mercaptocarboxylic acid, and/or 3-mercaptopropionic acid (3-MPA), as well as combinations comprising at least one of the foregoing.

In the absence of a sulfur containing promoter (such as 3-MPA), the reaction proceeds much slower and is less selective in producing bisphenol A (BPA). Thus, the use of a sulfur containing promoter can increase reaction conversion and improve selectivity. However, although the use of a sulfur containing promoter in the reaction is desirable for at least the above reasons, the use of such as promoter can generate sulfur containing byproducts, and can result in sulfur being present in the bisphenol A product stream(s) thereby resulting in a reduction in BPA purity. High purity levels are needed of the raw material BPA in order to manufacture high quality polycarbonate products. Such sulfur also could result in sulfur based noxious smells in the resulting BPA products, as well as in the polycarbonate end product. Potential degradation, as well as color worsening also could occur in the BPA monomer and resultant polycarbonate polymer as a result of sulfur impurities.

Figure 1:
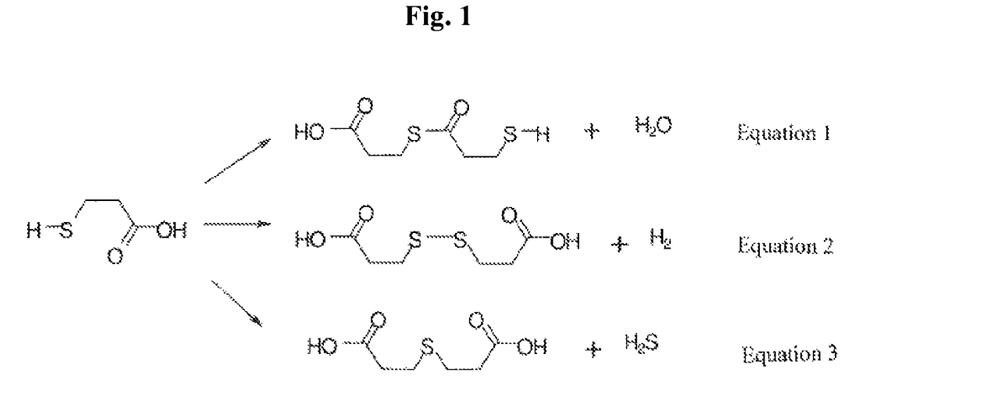
FIG. 1 depicts a schematic illustration of 3-MPA when used as a bulk promoter in a BPA ion exchange resin (IER) reaction can generate a series of by-products through side reactions.

In addition, sulfur compounds can be a source of odor issues during production of BPA and also during production of polycarbonate end products made from the BPA. A sulfur containing reaction promoter, such as 3-MPA, is an effective promoter for BPA production processes. However, if some of the promoter proceeds with the monomer into the resin process, it can also react with the phosgene, diphenyl carbonate, or the BPA during polycarbonate production and thus some sulfur can undesirably become incorporated into the polymer backbone and hence remain in the final product. Not to be limited by theory, it has been determined, for example, that when 3-MPA reacts with BPA it can create an end cap that would be incorporated into the polymer. The dimer or trimer of 3-MPA, as well as the sulfide and disulfide of 3-MPA also can be incorporated into the polymer chain. FIG. 1 depicts a schematic illustration showing that when 3-MPA is used as a bulk promoter in a BPA ion exchange resin (IER) reaction, the 3-MPA can generate a series of side reactions, such as those referred to as equation 1 (dimer or trimer of 3-MPA) and equations 2 and 3 (sulfide and disulfide, respectively). The majority of sulfur species present in the polycarbonate are bound to the polymer chain either as a chain building block or as an end cap, as opposed to being in a soluble state. Thus, during extrusion of polycarbonate the heat could generate a transesterification in the presence of moisture that could result in an undesirable release of odor through the release of 3-MPA or 3-MPA degradation products. Once the sulfur is incorporated into the BPA monomer, or incorporated into the polycarbonate polymer, the sulfur impurities cannot be removed by filtration or washing. Thus, a problem encountered is how to produce high purity BPA using effective reaction promoters, such as 3-MPA, while avoiding undesirable degradation of the BPA monomer and release of odor. It would be particularly desirable to obtain a method where sulfur could be removed downstream in the process, as opposed to being removed in the initial reaction section where phenol and acid can react together with a catalyst because in the initial reaction section sufficient amounts of sulfur are needed to execute the reaction. Moreover, it would be desirable to obtain such a method of sulfur removal wherein a promoter, such as 3-MPA, could be employed to achieve a high purity BPA product, while avoiding major restructuring of existing processing equipment.

Disclosed herein is a method to remove sulfur from a process stream comprising BPA such as a BPA product stream, in order to produce a high purity BPA product, specifically, how to, for example, remove sulfur impurities that have been incorporated into the BPA without destroying the monomer.

According to embodiments, and as described in further detail below, the addition of a base to the BPA product stream at elevated temperatures, such as temperatures greater than or equal to 50° C., typically between 80° C. and 100° C., can result in a significant reduction in organic sulfur concentration in the BPA. Thus, according to embodiments, sulfur is removed downstream in the BPA process, as opposed to removing sulfur in the reaction section. More particularly, sulfur can be removed from a molten stream comprising a crystallized adduct of BPA and phenol, where the sulfur is present at lower levels than in the upstream sections or initial reaction vessel of the process. Such removal of sulfur downstream in the process is beneficial for creating a high purity BPA product, as well as a high purity polycarbonate end product made from the purified BPA. Moreover, embodiments can employ a sulfur based promoter in the process and thus avoid complex adaptations and potential reconfigurations of processing equipment and processing parameters. Thus, processes can be tailored to existing BPA plants where sulfur containing promoters can be employed.

A BPA process 10 will now be described with reference to the exemplary and non-limiting process flow diagram depicted in FIG. 2. In a formulation vessel 12, a mixture can be made that is effective for conducting the reaction: acetone 14 and phenol 16 are present as reactants in stream 60 to form BPA (e.g., 2 moles of phenol and one mole of acetone can react to form BPA plus water). An excess of phenol can be present since phenol also can optionally serve as a solvent for the BPA. The sulfur containing reaction promoter 18 can be added in stream 62 to facilitate the reaction. The promoter 18 can be added, for example, at levels of greater than or equal to 500 parts per million by weight (ppm), specifically, 1,000 ppm to 4,000 ppm, based upon the weight of the whole formulation. The promoter 18 can comprise a sulfur containing promoter such as set forth above. The temperature in the formulation vessel can be greater than or equal to 50° C., for example.

The formulation can be fed, for example, continuously to the reaction section 20 where it is heated to greater than or equal to 70° C. In the reaction section 20, an acid catalyst (e.g., inorganic and organic acids, such as sulfuric acid and hydrogen chloride, and cationic exchange resins, ion-exchange-resin (IER) (e.g., an acidic condensation catalyst, such as sulfonic resin, sulfuric acid, hydrochloric acid)), for example, can be present to help catalyze the reaction. The result is that, for example, the concentration of phenol and acetone goes down, the acetone concentration can decrease close to zero and thus the concentration of BPA can increase. Isomers, which are undesired, also can form, which are organic molecules in which acetone and phenol have reacted to form other than BPA. The reaction can take place at above room temperature, for example, 60° C.

Optionally, a co-promoter can be added to the reaction section 20. In various embodiments, the co-promoter (e.g. additional promoter added into the reaction) is different than the initial promoter already added to the reaction above. Examples of co-promoters include the above described sulfur containing promoters (namely, 3-MPA, methyl mercaptan, ethyl mercaptan, 2,2-bis(methylthio)propane, mercaptocarboxylic acid (e.g., mercaptopropionic acid)), promoter-bound resins (including resins ionically-bound to quaternary amine groups contained in mercaptoalkylpyridines and/or mercaptoalkylamines, the latter including 2-mercaptoethylamine derived from hydrolysis of 2,2 dimethylthiozolidine), as well as combinations comprising at least one of any of the foregoing. The co-promoters can be present, for example, to enhance selectivity with some of the product being, for example, para para BPA (ppBPA), and to help obtain lower levels of the isomers.

The reaction mixture, which comprises acetone, phenol, BPA, sulfur and traces of isomers and promoter, can then flow in stream 66 to the crystallization section 22 where the mixture can be cooled to a temperature where crystals comprising BPA and phenol form. For example, the temperature can be less than or equal to 45° C. The crystals can be a BPA/phenol adduct. It is noted that "adduct" as used herein refers to the physical association of BPA and phenol (e.g., one molecule of BPA and one molecule of phenol can crystallize together to form a 1:1 molar ratio of BPA/phenol adduct).

Water 24 can optionally be added in stream 68 to the crystallization section 22, e.g., before crystallization to increase the rate of the crystallization process. The amount of water can be up to 3 weight percent (wt %), specifically, 0.1 to 3 wt % based upon a total weight of the mixture in the crystallization section 22. The stream exiting the crystallization section 22 (stream 70) can comprise a liquid phase and a solid phase.

In the filtration section 26, the liquid phase, stream 38 (e.g., mother liquor) can be separated from the solid phase, stream 80, which comprises the BPA/phenol crystals. Additional phenol from stream 27 and/or stream 32 can optionally be added to the filtration section 26 to wash the crystals.

Regarding the solid phase, this phase can comprise the BPA/phenol (PhOH) crystals, phenol, and traces of the isomers, and promoter. Typically, the solid phase, which is in the form of a slurry, can comprise, for example, up to 30 wt % of phenol. From the filtration section 26, the solid phase enters melting section 28 via slurry stream 80. Addition of phenol to the filtration section 26 also facilitates the melting of the crystals at a lower temperature.

Thus, this slurry stream 80 comprising the crystals can then become molten by heating (e.g., at 80° C.) in the melting section 28. The resulting molten stream can comprise a promoter, a solution of BPA in phenol, and possibly isomers. For example, the molten stream can comprise 50 wt % to 85 wt % BPA, specifically, 50 wt % to 75 wt % BPA, and more specifically, 55 wt % to 70 wt % BPA, based upon a total weight of the molten stream 82.

It has been determined that sulfur impurities can be removed from a stream comprising BPA and located downstream from an initial reaction section, e.g., a BPA product stream, instead of, for example, changing the sulfur containing promoter for an alternative technology. For example, a sulfur removal unit 54 could be located downstream of melting section 28 and upstream of a phenol desorption unit 30 (e.g., between the melting unit 28 and phenol desorption unit 30) without adversely affecting the other existing units or their operation. Therefore stream 82 exiting the melting section 28 can be directed to the sulfur removal unit 54. Since the molten stream 82 is at an elevated temperature, e.g., a temperature of greater than or equal to 70° C. to 120° C., the conditions are effective for sulfur removal while being sufficiently mild such that thermal degradation of the BPA is avoided.

Reduction of the concentration of sulfur impurities in the molten stream 82 comprises contacting the stream with a base in the sulfur removal unit 54. Employing the base treatment to molten stream 82, prior to the stream entering the phenol desorption unit 30 (e.g., evaporation unit), which is at a high temperature (e.g., greater than or equal to 200° C.) and under vacuum conditions, can be effective as the conditions prior to entering the desporption unit 30 are more mild and conducive to sulfur removal. More particularly, after the phenol is evaporated off in the desporption unit 30, a solid will be obtained or a product needing a higher temperature to remain liquid. In contrast, the BPA/phenol crystals can be melted and maintained molten, for example, at a temperature of 70° C. to 120° C., more specifically, 80° C. to 100° C. Under these mild conditions, the bases, e.g., resin bases, can remove the sulfur without becoming unstable and degrading. For example, generally, the resin bases are unstable and degrade when contacted with molten BPA at a temperature of greater than or equal to 200° C.

Figure 2:
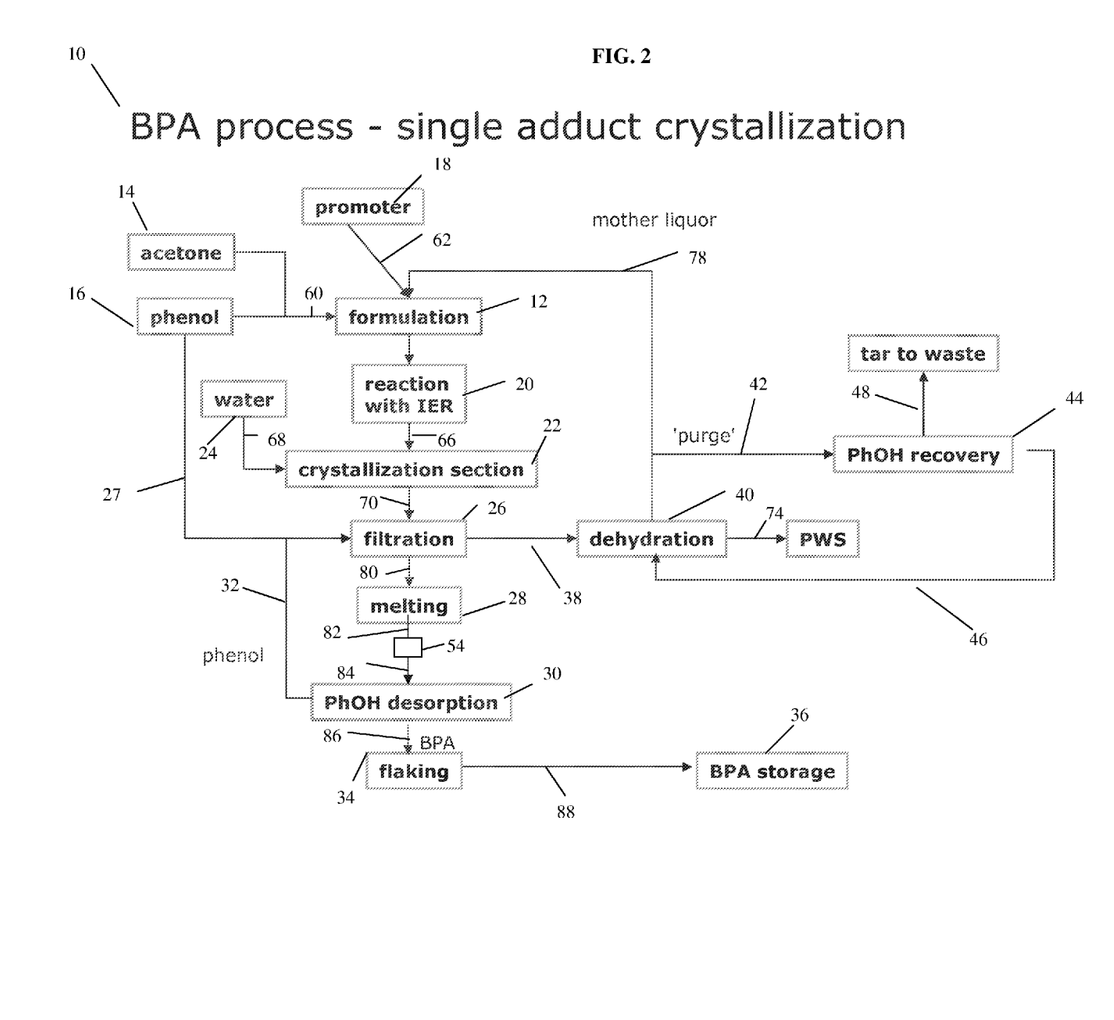
FIG. 2 depicts a BPA production process flow diagram using a single adduct crystallization.
Figure 3:
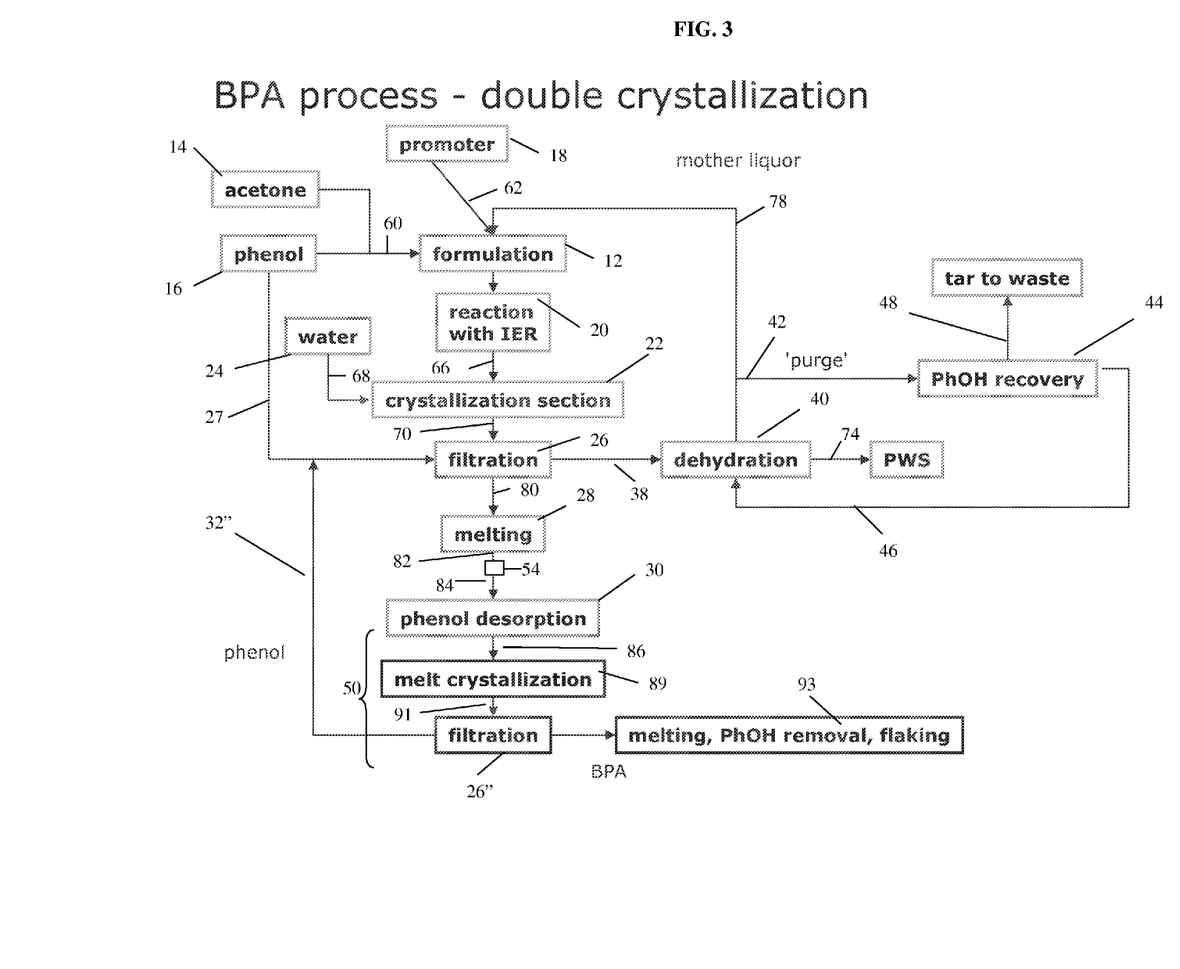
FIG. 3 depicts a BPA production process flow diagram using a double crystallization.
Figure 4:
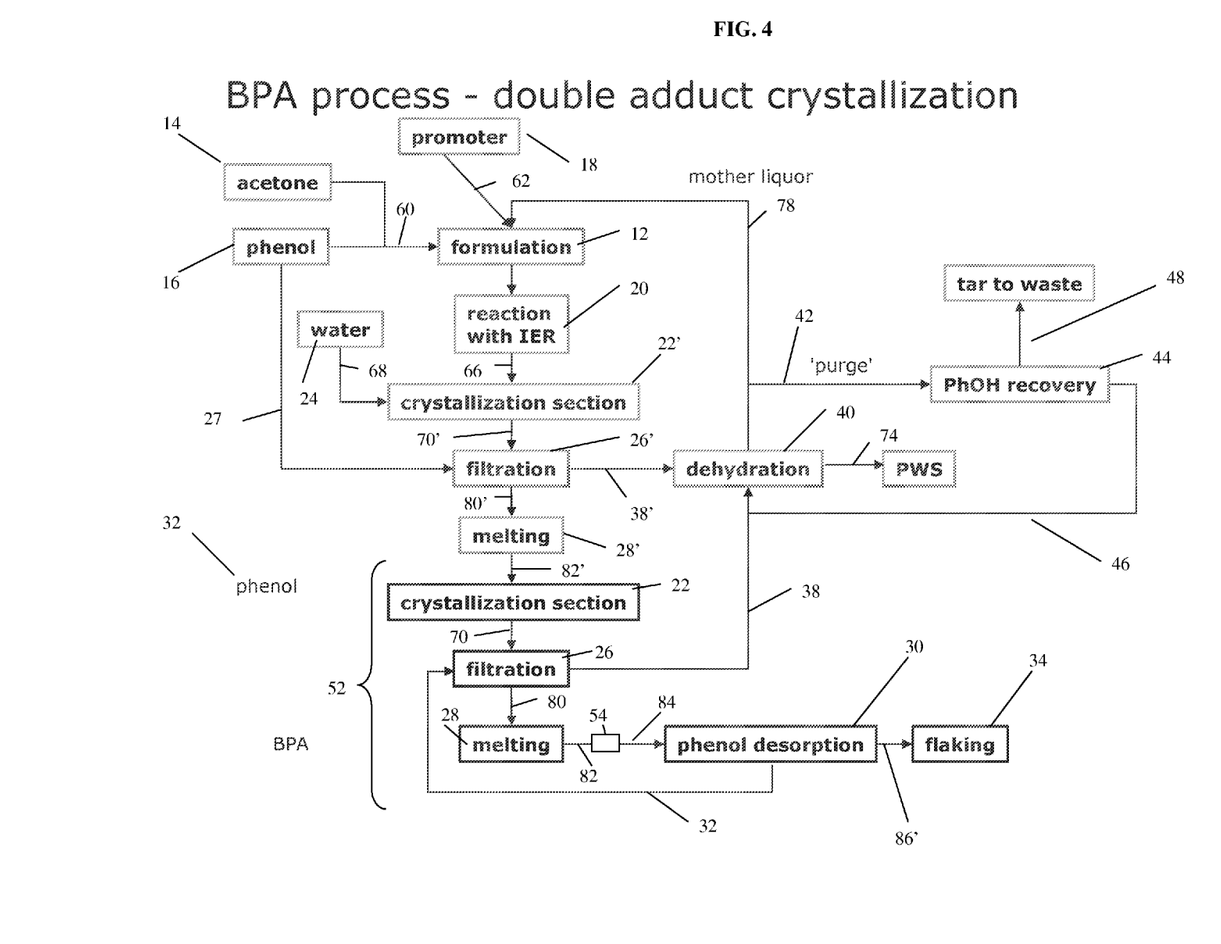
FIG. 4 depicts a BPA production process flow diagram using a double adduct crystallization.

Thus, molten stream 82, which comprises BPA, phenol, and sulfur, can enter the sulfur removal unit 54 located upstream from the desorption unit 30, as shown in FIGS. 2, 3 and 4. Optionally, the BPA of stream 82 can be dissolved in a solvent prior to treating the stream with a base. Examples of solvents include, but are not limited to, methanol, hexane, diethyl ether, carbon tetrachloride, tetrahydrofuran, chloroform, acetone, acetonitrile, additional phenol, and so forth, as well as combinations comprising at least one of the foregoing.

Optionally, an alkali solution, such as potassium hydroxide, sodium hydroxide, and/or other (earth)alkali metal hydroxide(s) can be added to the molten stream 82 to form a mixture, exiting the melting section 28 to form a mixture to enable the reduction of sulfur in the mixture. For example, the mixture can be treated at temperatures up to the solvent boiling temperature for a period of time, e.g., greater than 10 minutes. According to embodiments, a treatment temperature of 70° C. to 90° C. (e.g., using solvent such as methanol), with a contact time of greater than or equal to 8 hours can result in a 95% reduction in organic sulfur concentration in the BPA. However, other treatment temperatures and contact times are possible depending upon, for example, the phenol content.

Additionally, or alternatively, the molten stream 82 exiting the melting section 28 can be treated with an anion exchange resin (e.g., in addition or alternative to the alkali solution) as the base. The treatment can be, for example, at a temperature near the solvent boiling temperature and below the anion exchange resin operating temperature, e.g., until sufficient amount of sulfur has been removed. For example, the treatment temperature can be 70° C. to 120° C., specifically, 80° C. to 100° C., as described above. Examples of anion exchange resins include, but are not limited to, AMBERLYST* A21, which is a tert-amine divinely benzene/styrene ion exchange copolymer commercially available from Dow, Lewatit MP 62 WS, a weakly basic macroporous anion exchange resin with tertiary amine groups on crosslinked polystyrene (e.g., commercially available from Lanxess, Tulsion A-8XMP), a basic macroporous anion exchange resin with tertiary amine functionality attached to crosslinked polystyrene (e.g., commercially available from Thermax), and a combination comprising at least one of the foregoing. It is noted that although an alkali solution can reduce the sulfur content in the BPA, it has further been determined that when an anion exchange resin is employed as the base, the BPA quality and the color of the BPA is even better than when the alkali solution is employed.

The sulfur removal unit 54 can, for example, be a packed bed column filled with the anion exchange resin. The molten stream 82 exiting the melting unit 28 and comprising the molten BPA can pass through the column. The conditions, for example, can be a contact time of greater than or equal to 10 minutes, specifically greater than or equal to 1 hour, at a temperature of 70° C. to 120° C., more specifically, 80° C. to 100° C. It is noted that treatment with the base can be in a batch, semi-batch, or continuous process.

Treatment of the molten stream 82 can reduce the sulfur content in the final BPA product to less than or equal to 15 ppm sulfur, specifically, 0.5 to 15 ppm sulfur, more specifically, 1 to 7 ppm sulfur, yet more specifically, 1 to 5 ppm sulfur. For example, the final BPA product can have 2 to 10 ppm sulfur, 2 to 6 ppm sulfur, based upon the weight of the BPA product.

From the sulfur removal unit 54, a twelfth stream 84 comprising BPA and phenol can enter phenol desorption unit 30. Optionally, phenol can be recycled from the phenol desorption unit 30 to the initial phenol supply 16 and/or to the filtration unit 26. Product stream 86 can exit the phenol desorption unit 30 and optionally proceed for further processing and/or storage. For example, the product stream 86 can optionally be processed in flaking section 34 and/or sent to storage section 36 via stream 88.

Optionally, further processing of the various streams is possible, such as multiple crystallization cycles. For example, with reference to FIG. 4, the reaction mixture, which comprises acetone, phenol, BPA, sulfur and traces of isomers and promoter, can flow in stream 66 to the crystallization section 22' where the mixture can be cooled to a temperature where crystals comprising BPA and phenol form. For example, the temperature can be less than or equal to 45° C. Optionally, as noted above, water can be added to facilitate crystallization. From crystallization section 22, initial crystal stream 70', comprising a liquid phase and a solid phase, enters filtration section 26' where the liquid phase, stream 38' can be separated from the solid phase, stream 80'. Additional phenol from stream 27 and/or stream 32 can optionally be added to the filtration section 26' to wash the crystals.

The solid phase, stream 80' can then be melted in melting section 28' to form an initial molten stream 82'. This initial molten stream 82' can then be directed to the crystallization section 22 where it is crystallized and then further processed as described above. In such an arrangement, both liquid phase streams 38,38' can be directed to the dehydration section 40 and processed as described below.

FIG. 3 also illustrates a double crystallization, here, product stream 86 is further processed by directing the product stream 86 from the phenol desorption unit 30 into a melt crystallization unit 89 to form BPA crystals. The BPA crystals in phenol can be directed from the melt crystallization unit 89 via stream 91 to filtration unit 26" where phenol can optionally be removed and recycled via recycle stream 32", and stream 91 typically is in the form of a slurry (solid phase) comprising BPA crystals and phenol and can be further processed at section 93, e.g., melted, phenol removed, flaking, and/or storage.

The resultant BPA can be used in the production of BPA purified polycarbonate products. Accordingly, also disclosed in accordance with embodiments is a process of producing polycarbonate via in an interfacial or melt transesterification process. The polycarbonate can be formed into articles comprising reduced sulfur and characterized by virtually no sulfur based noxious smell.

With further reference to FIGS. 2, 3 and 4, the liquid phase in stream 38,38' can be processed in the dehydration section 40. From this section 40, a stream 74 comprising water can proceed into the phenol-water separation (PWS) unit while a ninth stream 78 comprising the mother liquor can exit the dehydration section 40 and be fed back into formulation vessel 12 and/or be purged (stream 42). Purge stream 42 can enter phenol recovery station 44 where phenol is recovered and recycled via stream 46 while a tar stream 48 exits the phenol recovery station 44 and proceed to waste.

The bisphenol A product from this process can be used to form polycarbonate, e.g., in an interfacial polymerization or melt polymerization process. Although the reaction conditions for interfacial polymerization can vary, an exemplary process generally involves dissolving or dispersing the bisphenol A in aqueous caustic material (e.g., aqueous caustic soda or potash), adding the resulting mixture to a water-immiscible solvent medium, and contacting the reactants with a carbonate precursor in the presence of a catalyst such as triethylamine and/or a phase transfer catalyst, under controlled pH conditions, e.g., about 8 to about 12. The most commonly used water immiscible solvents include methylene chloride, 1,2-dichloroethane, chlorobenzene, toluene, and the like.

Generally, in the melt polymerization process, polycarbonates can be prepared by co-reacting, in a molten state, the bisphenol A and a diaryl carbonate ester, such as diphenyl carbonate, in the presence of a transesterification catalyst in a Banbury* mixer, twin screw extruder, or the like to form a uniform dispersion. Volatile monohydric phenol is removed from the molten reactants by distillation and the polymer is isolated as a molten residue. A specifically useful melt process for making polycarbonates uses a diaryl carbonate ester having electron-withdrawing substituents on the aryls. Examples of specifically useful diaryl carbonate esters with electron withdrawing substituents include bis(4-nitrophenyl) carbonate, bis(2-chlorophenyl)carbonate, bis(4-chlorophenyl)carbonate, bis(methyl salicyl)carbonate, bis(4-methylcarboxylphenyl) carbonate, bis(2-acetylphenyl) carboxylate, bis(4-acetylphenyl) carboxylate, or a combination comprising at least one of the foregoing esters. Examples of transesterification catalysts include tetrabutylammonium hydroxide, methyltributylammonium hydroxide, tetrabutylammonium acetate, tetrabutylphosphonium hydroxide, tetrabutylphosphonium acetate, tetrabutylphosphonium phenolate, or a combination comprising at least one of the foregoing.

In one embodiment, a process for producing a bisphenol A product comprises: reacting phenol with acetone in the presence of a sulfur containing promoter to obtain a reaction mixture comprising bisphenol A, phenol, and the promoter; after reacting the phenol with the acetone in the presence of the promoter, cooling the reaction mixture to form a crystal stream comprising crystals of bisphenol A and phenol (e.g., that contain sulfur); separating the crystals from the crystal steam; melting the crystals to form a molten stream of bisphenol A, phenol, and sulfur (e.g., promoter, sulfur containing by-products, etc.); contacting the molten stream with a base to reduce a sulfur concentration in the molten stream and form a reduced sulfur stream; and removing phenol from the reduced sulfur stream to form a bisphenol A product.

In the various embodiments, (i) the molten stream can be contacted with a base at a temperature of 70° C. to 120° C.; and/or (ii) the molten stream can be contacted with a base at a temperature of 80° C. to 100° C.; and/or (iii) the promoter can comprise a catalyst selected from 3-mercaptopropionic acid, methyl mercaptan, ethyl mercaptan, 2,2-bis(methylthio)propane, mercaptocarboxylic acid, and combinations comprising at least one of the foregoing promoters; and/or (iv) the promoter can comprise 3-mercaptopropropionic acid; and/or (v) the base can comprise an alkali solution; and/or (vi) the base can comprise an anion exchange resin; and/or (vii) the anion exchange resin comprises a tert-amine divinylbenzene/styrene ion exchange copolymer; and/or (viii) the process can further comprise adding additional phenol to the molten stream prior to contacting the stream with the base; and/or (ix) the sulfur concentration can be reduced to 0.5 ppm to 15 ppm based upon the weight of the bisphenol A; and/or (x) the sulfur concentration can be reduced to 2 ppm to 10 ppm based upon the weight of the bisphenol A; and/or (xi) the sulfur concentration can be reduced to 3 ppm to 8 ppm based upon the weight of the bisphenol A; and/or (xii) the process can further comprise, prior to forming the crystal stream, cooling the reaction mixture to form an initial crystal stream comprising initial crystals of bisphenol A and phenol, separating the initial crystals from the initial crystal steam, melting the initial crystals to form an initial molten stream, and then performing the cooling to form the crystal steam; and/or (xiii) the process can further comprise melt crystallizing the bisphenol A product.

Also included herein is polycarbonate made from the bisphenol A product of any of the above processes, as well as products made from the polycarbonate.

In one embodiment, a process for making polycarbonate, comprises: reacting, in the presence of a transesterification catalyst, a diaryl carbonate ester and the bisphenol A product formed in any of the above methods, wherein the bisphenol A has a sulfur concentration of 1 ppm to 15 ppm, based upon a weight of the bisphenol A.

In another embodiment, a process for making polycarbonate, comprises: forming a mixture of the bisphenol A product from any of the above methods, in aqueous caustic material, wherein the bisphenol A has a sulfur concentration of 1 ppm to 15 ppm, based upon a weight of the bisphenol A; adding the mixture to a water-immiscible solvent medium; and contacting the reactants with a carbonate precursor in the presence of a catalyst to form the polycarbonate.

The polycarbonate can be formed into a container such as a bottle, bowl, storage container, pan, and so forth. Since the polycarbonate has a reduced sulfur concentration, yet was formed from a bisphenol A that was produced using a sulfur containing promoter, the process is efficient, yet the final product has reduced (e.g., does not release) sulfur odors and has greater commercial viability. This polycarbonate container can be particularly useful for use with containers that are exposed to conditions that could release the sulfur, e.g., that may be heated (such as a food storage container being heated in a microwave, a pan being heated in the oven, a water bottle being heated in a vehicle in the sun, etc.). The specific design (e.g., shape and size) of the container is not limited.

In various embodiments, the container can be a medicine, food, or beverage container such as a bottle, e.g., a water bottle. Examples of bottles include a baby bottle, beverage bottle (e.g., juice bottle, water bottle, carbonated drink bottle, alcoholic beverage bottle), medical bottle, and personal care bottle. The beverage bottle can, for example, be a bottle having a capacity of two liters, a capacity of 20 ounces, a capacity of 16.9 ounces, a capacity of 12 ounces, a capacity of 6 ounces, a capacity of 4 ounces, or a filled weight of 200 to 800 grams.

These bottles can be formed by various processes, depending upon the particular polycarbonate (e.g., molecular weight), and the desired container. Examples of processes for forming the container include injection molding and blow molding (e.g., injection blow molded, injection stretch blow molded, extrusion blow molded, and extrusion stretch blow molded).

In an embodiment, a container can comprise a polycarbonate formed from a bisphenol A having a sulfur concentration of 0.5 to 15 ppm based upon a weight of the bisphenol A. In the various embodiments of the container, (i) the sulfur concentration is 1 ppm to 15 ppm based upon the weight of the bisphenol A; and/or (ii) the sulfur concentration is 2 ppm to 10 ppm based upon the weight of the bisphenol A; and/or (iii) the sulfur concentration is 3 ppm to 8 ppm based upon the weight of the bisphenol A; and/or (iv) the sulfur concentration is 1 ppm to 7 ppm based upon the weight of the bisphenol A; and/or (v) the container is a bottle; and/or (vi) the bisphenol A was formed using a sulfur containing promoter.

The following non-limiting examples further illustrate embodiments disclosed herein.

EXAMPLES

Example 1

As can be seen from the data set forth in Table 1 below, the sulfur level in a BPA sample having a para para (pp) BPA purity of 99.598 weight percent can be reduced from 23 ppm sulfur based upon the total weight of BPA down to 8 ppm with the addition of a strong base, potassium hydroxide (KOH). As shown in Table 1, the purity level decreased by only 0.367, while the sulfur decreased by 15 ppm. Table 1 further shows that when an anion exchange resin (AEX) was added instead of the KOH, even further improvements in purity and reduction in sulfur level resulted. In particular, treating the BPA having an initial ppBPA organic purity of 99.598 weight percent with the resin bound base (anion exchange resin, AEX) resulted in a ppBPA purity of 99.526 weight percent, which is a reduction in purity of only 0.072, and a sulfur reduction from 23 ppm down to 3 ppm based on BPA, which is a 20 ppm reduction in sulfur.

The experimental conditions were carried out as follows. For each treatment, 0.5 grams of BPA flakes were dissolved in 5 milliliters (ml) of high performance liquid chromatography (HPLC) grade methanol in a 25 ml glass sample preparation vial. A heating block was used for temperature control.

The following treatments were applied: Sample 1 was capped and heated at 80° C. for 6 hours. To Sample 2, 1 ml of 10% mass/volume (w/v) potassium hydroxide (KOH) in methanol was added before capping and heating at 80° C. for 6 hours. To Sample 3, 2 grams (g) of Rohm & Haas AMBERLYST* A-21 anion exchange beads ("A-21 resin") were added before capping and heating at 80° C. for 6 hours. After the heating, the samples were allowed to cool before filtering (0.45 micrometers (μm)) into a fresh sample prep vial. Next, 10 ml of methanol was used to wash the used vial and beads left in the filtration syringe. The washings were then collected. All samples were then evaporated at 80° C. for 5 hours under a stream of nitrogen.

TABLE 1

|  |  | BPA Sample 1 | BPA KOH Sample 2 | BPA AEX Sample 3 |
|---|---|---|---|---|
| ppBPA | (% wt.) | 99.598 | 99.231 | 99.526 |
| SULFUR | (ppm) | 23 | 8 | 3 |

Example 2

Table 2, which is explained in further detail below, sets forth further data demonstrating the significant reduction in sulfur (S) achievable, according to embodiments.

TABLE 2

| sample | A-21 resin grams | BPA grams | PhOH grams | total grams | BPA % wt. | total S start ppm | total S after ppm | S removed % | temp ° C. | time hours | water % | catalyst state |
|---|---|---|---|---|---|---|---|---|---|---|---|---|
| 4 | 2.077 | 4.069 | 6.010 | 10.079 | 40.4 | 7.9 | 3.1 | 61 | 86 | 1 | 0 | wet |
| 5 | 2.008 | 4.122 | 6.070 | 10.192 | 40.4 | 7.9 | 2.8 | 65 | 86 | 2 | 0 | wet |
| 6 | 2.016 | 4.065 | 6.020 | 10.085 | 40.3 | 7.9 | 3.0 | 62 | 86 | 3 | 0 | wet |
| 7 | 1.516 | 4.006 | 6.060 | 10.066 | 39.8 | 7.8 | 3.3 | 58 | 86 | 2 | 0 | wet |
| 8 | 1.052 | 4.102 | 6.010 | 10.112 | 40.6 | 8.0 | 3.7 | 53 | 86 | 1 | 0 | wet |
| 9 | 1.023 | 4.228 | 6.030 | 10.258 | 41.2 | 8.1 | 3.1 | 62 | 86 | 3 | 0 | wet |
| 10 | None | 4.020 | 6 | 10.020 | 40.1 | 7.9 | 8.1 | −3 | 86 | 2 | 0 | — |
| 11 | None | 4.005 | 6 | 10.005 | 40.0 | 7.8 | 8.0 | −2 | 86 | 2 | 0 | — |
| 12 | None | 10 | — | 10 | 100.0 | 19.6 |  |  |  |  | 0 | — |
| 13 | 0.11 | 5.51 | 4.54 | 10.05 | 54.8 | 12.6 | 3.0 | 76 | 100 | 6 | 0 | dry |
| 14 | 0.06 | 5.52 | 4.51 | 10.03 | 55.1 | 12.7 | 8.7 | 31 | 100 | 6 | 0 | dry |
| 15 | 0.06 | 5.53 | 4.56 | 10.09 | 54.8 | 12.6 | 6.7 | 47 | 100 | 6 | 0 | dry |
| 16 | 0.21 | 5.54 | 4.50 | 10.04 | 55.1 | 12.7 | 8.1 | 36 | 100 | 6 | 0 | dry |
| 17 | 0.10 | 5.50 | 4.55 | 10.05 | 54.7 | 12.6 | 8.9 | 29 | 100 | 6 | 0 | dry |
| 18 |  | 10 |  | 10 | 100.0 | 23 |  |  |  |  |  |  |
| 19 | 0.06 | 4.00 | 4.70 | 8.70 | 46.0 | 10.5 | 4.4 | 58 | 100 | 6 | 10 | dry |
| 20 | 0.06 | 4.20 | 4.10 | 8.30 | 50.6 | 11.6 | 4.1 | 65 | 100 | 6 | 10 | dry |

TABLE 2-continued

| sample | A-21 resin grams | BPA grams | PhOH grams | total grams | BPA % wt. | total S start ppm | total S after ppm | S removed % | temp °C. | time hours | water % | catalyst state |
|---|---|---|---|---|---|---|---|---|---|---|---|---|
| 21 | 0.10 | 3.90 | 3.80 | 7.70 | 50.6 | 11.6 | 3.9 | 66 | 100 | 6 | 10 | dry |
| 22 | 0.10 | 4.60 | 5.20 | 9.80 | 46.9 | 10.7 | 4.9 | 54 | 100 | 6 | 10 | dry |
| 23 | 0.21 | 4.00 | 3.60 | 7.60 | 52.6 | 12.0 | 3.8 | 68 | 100 | 6 | 10 | dry |
| 24 | 0.21 | 3.40 | 3.40 | 6.80 | 50.0 | 11.4 | 3.4 | 70 | 100 | 6 | 10 | dry |
| 25 | 0.21 | 5.00 | 5.40 | 10.40 | 48.1 | 11.0 | 5.2 | 53 | 100 | 6 | 10 | dry |
| 26 | | 10.20 | 11.40 | 21.60 | 47.2 | 10.8 | 10.8 | 0 | 100 | 6 | 10 | — |

Samples 4 to 11 used the same BPA source as that of the BPA Sample 12, which included 19.6 ppm total sulfur, as indicated in Table 2. The starting sulfur content was calculated for each sample from the mixture composition of BPA and phenol, and the 19.6 ppm sulfur that had been determined in the BPA source. The PhOH was sulfur free.

Similarly, Samples 13 to 17 used the same BPA source as that of the BPA Sample 18, which included 23 ppm total sulfur, as indicated in Table 2. The starting sulfur content also was calculated from the mixture composition of BPA and phenol, and the 23 ppm sulfur that had been determined in the BPA source. The PhOH also was sulfur free in these samples.

Samples 19 to 26 used the same BPA source as each other. A sample of the mixture of Sample 26 was analyzed for sulfur. The 10.8 ppm sulfur content of this mixture (Sample 26) was used to calculate starting values for the sulfur content for Samples 19 to 25, which were made from the same BPA, as well as PhOH source.

It is noted that the total sulfur amounts after treatment were determined experimentally, as further described below.

The following procedure of the sulfur removal experiments in the presence of ion exchange resin, A-21, was applied. Before using the A-21 resin for the sulfur removal experiments, the material was thoroughly washed with demineralized water. A conductivity measurement was conducted on the effluent after each treatment and the resin was released when the conductivity measured less than or equal to 20 microsiemens per centimeter ($\mu$S/cm).

As it could be difficult to control the moisture content (70 to 90 wt %) in the wet A-21 resin, part of the material was also dried and used in separate tests with water addition. The amount of water typically added was 10 wt % based upon the total weight of BPA and phenol.

Sample Preparation and Test Conditions

In a 25 ml glass vial, the A-21 resin was added first, followed by BPA and phenol. In the first series, wet A-21 resin was used for the sulfur removal. After preparation of the mixture of A-21 resin, BPA and phenol, the 25 ml vial was closed and exposed to 86° C. in a preheated oven for 1, 2, or 3 hours.

In the second series, dried A-21 resin was used for the sulfur removal. After preparation of the mixture of A-21 resin, BPA, and phenol, water was then added before the 25 ml vial was closed and exposed to 100° C. in a preheated oven for 6 hours.

The different exposure conditions for wet and dried resins were applied because the different water concentrations resulted in different behavior to completely melt the mixture of BPA and phenol.

The Total Sulfur Measurement

The total sulfur measurement was based on the destruction of a 40 milligram (mg) sample at 1100° C. The vapors emanating from the sample during the destruction were led through a scrubber followed by a fluorescence detector with a flow of argon and oxygen. Under these conditions, the sulfur was converted into sulfur dioxide ($SO_2$). The total sulfur concentration in the original 40 mg sample was determined based on the response of the fluorescence detector.

The BPA organic purity can be defined as 100 wt % minus the sum of known and unknown impurities detected using ultraviolet (UV) (see HPLC method in Nowakowska et al., Polish J. Appl. Chem., XI (3), 247-254 (1996)).

As can be seen from the data set forth in Table 2, specifically regarding Samples 4 to 9, when a mixture of BPA and PhOH is molten and treated with the basic ion exchange resin, a significant amount of the sulfur is removed. However, in the absence of the resin and under otherwise the same experimental conditions, the same heat treatment does not result in a reduction of the sulfur level (see Samples 10 and 11 where no resin was employed and no reduction in sulfur resulted). In these experiments the catalyst was undried and contained some humidity.

Samples 13 to 17 show that also at much lower levels of basic ion exchange resins and higher levels of BPA, sulfur can be effectively removed in significant amounts. In these experiments, the ion exchange resin had been dried before use. The BPA content of these samples was in a practical range that also can be encountered in the plant stream at reference 54 (FIGS. 2-4): 45 to 70 wt %, for example.

Samples 19 to 25 repeat these experiments, but now in the presence of 10 wt % water. Also in these cases, a significant amount of sulfur was removed, as shown in Table 2.

Examples 1-2 demonstrate that the addition of a base is effective in significantly reducing the amount of sulfur present in BPA, and thus is effective in enabling the production of high quality BPA, as well as high quality polycarbonate made from the resultant BPA. Such products also can be characterized by a reduction or elimination of noxious smell and enhanced color due to the low levels of sulfur achievable, according to embodiments.

In general, the embodiments may alternately comprise, consist of, or consist essentially of, any appropriate components herein disclosed. The embodiments may additionally, or alternatively, be formulated so as to be devoid, or substantially free, of any components, materials, ingredients, adjuvants or species used in prior art compositions or that are otherwise not necessary to the achievement of the function and/or objectives of the embodiments herein.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). All amounts disclosed herein for the compositions do not exceed 100 wt %. "Combination" is inclusive of blends, mixtures, alloys, reaction products, and the like. Furthermore, terms "first," "second,", "initial", and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A process for producing a bisphenol A product comprising:
    reacting phenol with acetone in the presence of a sulfur containing promoter to obtain a reaction mixture comprising bisphenol A, phenol, and the promoter;
    after reacting the phenol with the acetone, cooling the reaction mixture to form a crystal stream comprising crystals of bisphenol A and phenol;
    separating the crystals from the crystal steam;
    melting the crystals to form a molten stream of bisphenol A, phenol, and sulfur;
    contacting the molten stream with a base to reduce a sulfur concentration in the molten stream and form a reduced sulfur stream; and
    removing phenol from the reduced sulfur stream to form a bisphenol A product.

2. The process according to claim 1, wherein the base comprises an alkali solution.

3. The process according to claim 1, further comprising adding additional phenol to the molten stream prior to contacting the stream with a base.

4. The process according to claim 1, wherein the molten stream is contacted with the base at a temperature of 70° C. to 120° C.

5. The process according to claim 4, wherein the temperature is 80° C. to 100° C.

6. The process according to claim 1, wherein the promoter comprises a catalyst selected from 3-mercaptopropionic acid, methyl mercaptan, ethyl mercaptan, 2,2-bis(methylthio)propane, mercaptocarboxylic acid, and combinations comprising at least one of the foregoing promoters.

7. The process according to claim 6, wherein the promoter comprises 3-mercaptopropionic acid.

8. The process according to claim 1, wherein the base comprises an anion exchange resin.

9. The process according to claim 8, wherein the anion exchange resin comprises a tert-amine divinylbenzene/styrene ion exchange copolymer.

10. The process according to claim 1, wherein the sulfur concentration is reduced to 0.5 ppm to 15 ppm based upon the weight of the bisphenol A.

11. The process according to claim 10, wherein the sulfur concentration is reduced to 2 ppm to 10 ppm based upon the weight of the bisphenol A.

12. The process according to claim 11, wherein the sulfur concentration is reduced to 3 ppm to 8 ppm based upon the weight of the bisphenol A.

13. The process according to claim 1, further comprising, prior to forming the crystal stream,
    cooling the reaction mixture to form an initial crystal stream comprising initial crystals of bisphenol A and phenol;
    separating the initial crystals from the initial crystal steam;
    melting the initial crystals to form an initial molten stream; and
    then performing the cooling to form the crystal steam according to claim 1.

14. The process according to claim 13, further comprising melt crystallizing the bisphenol A product.

15. A process for making polycarbonate, comprising:
    reacting phenol with acetone in the presence of a sulfur containing promoter to obtain a reaction mixture comprising bisphenol A, phenol, and the promoter;
    after reacting the phenol with the acetone, cooling the reaction mixture to form a crystal stream comprising crystals of bisphenol A and phenol;
    separating the crystals from the crystal steam;
    melting the crystals to form a molten stream of bisphenol A, phenol, and sulfur;
    contacting the molten stream with a base to reduce a sulfur concentration in the molten stream and form a reduced sulfur stream;
    removing phenol from the reduced sulfur stream to form a bisphenol A product; and
    reacting, in the presence of a transesterification catalyst, a diaryl carbonate ester and the bisphenol A product.

16. A process for making polycarbonate, comprising:
    reacting phenol with acetone in the presence of a sulfur containing promoter to obtain a reaction mixture comprising bisphenol A, phenol, and the promoter;
    after reacting the phenol with the acetone, cooling the reaction mixture to form a crystal stream comprising crystals of bisphenol A and phenol;
    separating the crystals from the crystal steam;
    melting the crystals to form a molten stream of bisphenol A, phenol, and sulfur;
    contacting the molten stream with a base to reduce a sulfur concentration in the molten stream and form a reduced sulfur stream;
    removing phenol from the reduced sulfur stream to form a bisphenol A product;
    forming a mixture of the bisphenol A product in aqueous caustic material;
    adding the mixture to a water-immiscible solvent medium; and
    contacting the reactants with a carbonate precursor in the presence of a catalyst to form the polycarbonate.

17. A container, comprising the polycarbonate from claim 16.

18. A container, comprising a polycarbonate formed from a bisphenol A having a sulfur concentration of 0.5 ppm to 15 ppm based upon the weight of the bisphenol A.

19. The container according to claim 18, wherein the container is a food container.

20. The container according to claim 18, wherein the bisphenol A was formed using a sulfur containing promoter.

21. The container according to claim 18, wherein the sulfur concentration is to 2 ppm to 10 ppm based upon the weight of the bisphenol A.

22. The container according to claim 21, wherein the sulfur concentration is 3 ppm to 8 ppm based upon the weight of the bisphenol A.

23. The container according to claim 18, wherein the container is a bottle.

24. The container according to claim 23, wherein the bottle is selected from a baby bottle, beverage bottle, medical bottle, and personal care bottle.

25. The container according to claim 24, wherein the bottle is a beverage bottle selected from a juice bottle, water bottle, carbonated drink bottle, alcoholic beverage bottle.

26. The container according to claim 24, wherein the bottle is a beverage bottle selected from bottles having a capacity of two liters, a capacity of 20 ounces, a capacity of 16.9 ounces, a capacity of 12 ounces, a capacity of 6 ounces, and/or a filled weight of 200 to 800 grams.

* * * * *